United States Patent
Sabesan et al.

(10) Patent No.: US 8,524,925 B2
(45) Date of Patent: Sep. 3, 2013

(54) PRODUCTION OF FURFURAL FROM BIOMASS

(75) Inventors: Subramaniam Sabesan, Wilmington, DE (US); Christina Jacy Spado, Philadelphia, PA (US)

(73) Assignee: E I du Pont de Nemours and Company, Wilmington, DE (US)

(*) Notice: Subject to any disclaimer, the term of this patent is extended or adjusted under 35 U.S.C. 154(b) by 30 days.

(21) Appl. No.: 13/285,745

(22) Filed: Oct. 31, 2011

(65) Prior Publication Data
US 2013/0109869 A1    May 2, 2013

(51) Int. Cl.
*C07D 307/50* (2006.01)

(52) U.S. Cl.
USPC ........................................... 549/489

(58) Field of Classification Search
USPC ........................................... 549/489
See application file for complete search history.

(56) References Cited

U.S. PATENT DOCUMENTS

| | | | |
|---|---|---|---|
| 7,829,732 B2 * | 11/2010 | Mascal | 549/483 |
| 2008/0033187 A1 | 2/2008 | Zhao et al. | |
| 2010/0317879 A1 | 12/2010 | Zhao et al. | |
| 2011/0071306 A1 | 3/2011 | Robinson | |

OTHER PUBLICATIONS

Reichardt, Solvents and Solvent Effects in Organic Chemistry, 2003, Verlag GmbH &Co., 3rd ed., p. 471-507.*
E.I. Fulmer et al., The Production of Furfural From Xylose Solutions by Means of Hydrochloric Acid-Sodium Chloride Systems, Department of Chemistry, Iowa, Journal of Physical Chemistry, vol. 40 (1936), pp. 133-141.
C. Liu et al. The Enhancement of Xylose Monomer and Xylotriose Degradation by Inorganic Salts in Aqueous Solutions at 180oC, Carbohydrate Research, vol. 341 (2006), pp. 2850-2556.
G. Marcotullio et al., Chloride Ions Enhance Furfural Formation From D-Xylose in Dilute Aqueous Acidic Solutions, Green Chemistry (2010), The Royal Society of Chemistry, pp. 1-8.
F. Tao et al., Efficient Process for the Conversion of Xylose to Furfural With Acidic Ionic Liquid, Can. J. Chem., vol. 89, (2011), pp. 83-87.
International Search Report, PCT International Application No. PCT/US2012/057820, Mailed Mar. 26, 2013.

* cited by examiner

*Primary Examiner* — Taylor Victor Oh

(57) ABSTRACT

Processes for producing furfural from biomass are provided. The processes use a metal halide in aqueous solutions of water-miscible and can provide a furfural yield of greater than 70%.

13 Claims, 1 Drawing Sheet

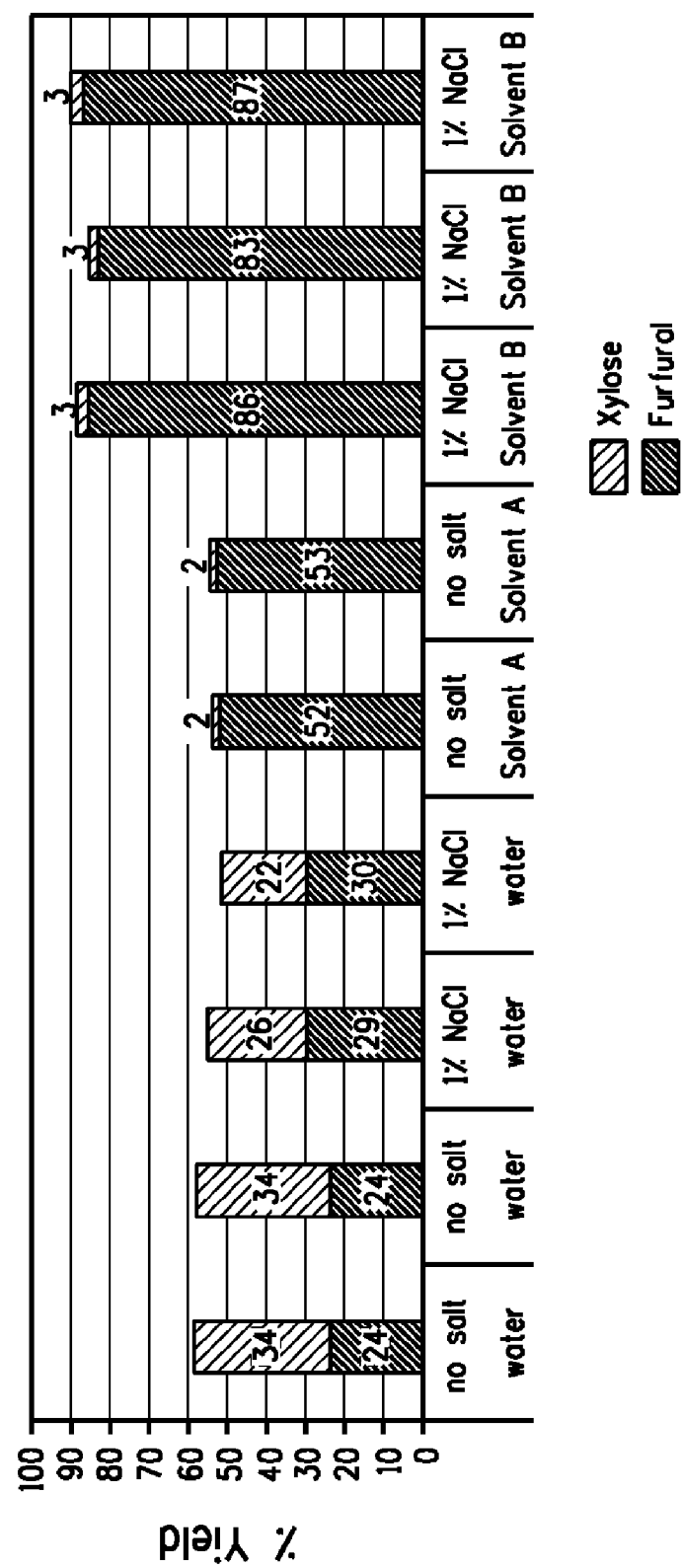

US 8,524,925 B2

PRODUCTION OF FURFURAL FROM BIOMASS

FIELD OF THE INVENTION

A method for the production of furfural from biomass is provided.

BACKGROUND

Furfural and related compounds are useful precursors and starting materials for industrial chemicals for use as pharmaceuticals, herbicides, stabilizers, and polymers. Conventionally, furfural can be produced from $C_5$ sugars which have been obtained from hydrolysis of the hemicellulose contained in biomass. Typically, the hydrolysis of biomass is performed with aqueous acids at relatively high temperatures to obtain $C_5$ and $C_6$ sugars derived from xylan and glucan, respectively.

US Patent Publication No. 20110071306 discloses a method for the acid hydrolysis of carbohydrates in or from biomass, using a solvent system including an aqueous ether, where the ether forms a majority of the system.

In the biomass to furfural conversion process, it is known that metal halides can increase the rate of xylose decomposition, though without an increased furfural yield, especially when carried out in an aqueous medium. In the presence of ionic liquids, high metal salt loading (10%) increased yield enhancement has been reported for the conversion of fructose and glycose to hydroxymethyl furfural There remains a need for a process that converts biomass to furfural, or xylose to furfural, at both increased rate and increased yield. It would also be desirable to prevent decomposition of the furfural once it is formed by such a process. Finally, it would be beneficial to reduce the large volume of acid currently used because of potential environmental and handling issues.

SUMMARY OF THE INVENTION

A process is provided comprising:
  a) providing an aqueous solution comprising metal halide, water-miscible organic solvent, mineral acid, and water
  b) providing a feedstock comprising at least one of the following:
    i) lignocellulosic feedstock containing glucan and xylan,
    ii) hemicellulosic material,
    iii) $C_5$ sugar monomers and $C_5$ oligomers;
  c) contacting the feedstock with the aqueous solution to form a reaction mixture, wherein
    i) the concentration of water-miscible organic solvent is within the range from about 10 weight percent to about 80 weight percent,
    ii) the concentration of metal halide is from about 0.1 weight percent to about 2 weight percent,
    iii) the mineral acid concentration is from about 0.5 to about 4 weight percent; and
    iv) the feedstock is present at about 1 to about 50 weight percent,
  wherein the weight percentages are based on the total weight of the reaction mixture;
and
  d) heating the reaction mixture at a temperature in the range of about 140° C. to about 190° C. for a time sufficient to effect a reaction to produce furfural, wherein the aqueous solution remains monophasic at the reaction temperature and at the completion of the reaction.

BRIEF DESCRIPTION OF THE FIGURE

FIG. 1 shows a comparison of furfural yield obtained with various solvent systems, according to Example 1.

DETAILED DESCRIPTION

Definitions

As used herein, where the indefinite article "a" or "an" is used with respect to a statement or description of the presence of a step in a process disclosed herein, unless the statement or description explicitly provides to the contrary, the use of such indefinite article does not limit the presence of the step in the process to one in number.

As used herein, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

As used herein, the term "about" modifying the quantity of an ingredient or reactant employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities. The term "about" may mean within 10% of the reported numerical value, preferably within 5% of the reported numerical value.

As used herein, the term "biomass" refers to any hemicellulosic or lignocellulosic material and includes materials comprising hemicellulose, and optionally further comprising cellulose, lignin, starch, oligosaccharides and/or monosaccharides.

As used herein, the term "lignocellulosic" means, comprising cellulose, lignin and hemicellulose.

As used herein, the term "hemicellulosic" refers to a material comprising $C_5$ and $C_6$ sugar polymers. Hemicellulose consists of short, highly branched chains of sugars. In contrast to cellulose, which is a polymer of only glucose, a hemicellulose is a polymer of five different sugars. It contains five-carbon sugars (usually D-xylose and L-arabinose) and six-carbon sugars (D-galactose, D-glucose, and D-mannose) and uronic acid. The sugars are partially acetylated. Typically the acetyl content is 2 to 3% weight of hemicellulose.

The relative content of $C_5$ versus $C_6$ sugars produced from hemicellulose depends on the source of the hemicellulose. When hydrolyzed, the hemicellulose from hardwoods releases products high in xylose (a five-carbon sugar). The hemicellulose contained in softwoods, by contrast, yields more six-carbon sugars. The branched nature of hemicellulose renders it amorphous and relatively easy to hydrolyze to its constituent sugars compared to cellulose.

As used herein, the term "miscible" refers to a mixture of components that, when combined, form a single phase (i.e., the mixture is "monophasic") under specified conditions (e.g., component concentrations, temperature).

As used herein, the term "monophasic" refers to a reaction medium that includes only one liquid phase. Some examples are water, aqueous solutions, and solutions containing aqueous and organic solvents that are miscible with each other. The term "monophasic" can also be used to describe a method employing such a reaction medium.

As used herein, the term "biphasic" refers to a reaction medium that includes two immiscible liquid phases, for example, an aqueous phase and a water-immiscible organic solvent phase. The term "biphasic" can also be used to describe a method employing such a reaction medium.

As used herein the term "water-miscible organic solvent" refers to an organic solvent that can form a monophasic solution with water at the temperature at which the reaction is carried out.

As used herein, the term "metal halide" refers to a compound generally described by the formula $MX_n$, where M is a metal cation of valence +n, X is a halogen, and n ranges from +1 to +3.

Unless otherwise defined, all technical and scientific terms used herein have the same meaning as commonly understood by one of ordinary skill in the art to which this invention belongs. In case of conflict, the present specification, including definitions, will control.

In the processes disclosed herein, a feedstock is contacted with water in the presence of a solution of: a mineral acid, a water-miscible organic solvent, and a metal halide, to produce a reaction mixture that, under suitable reaction conditions, produces a mixture comprising furfural.

The feedstock is present in the reaction mixture at about 0.1 weight percent to about 50 weight percent based on the weight of the reaction mixture. In some embodiments, the feedstock is present in the reaction mixture at a weight percentage between and optionally including any two of the following values: 0.1, 5, 10, 15, 20, 25, 30, 35, 40, 45, and 50 weight percent. The feedstock comprises at least one of the following materials: lignocellulosic feedstock containing glucan and xylan; hemicellulosic material; and $C_5$ sugar monomers and $C_5$ oligomers. Useful ranges of solids loading are dependent on the viscosity of the feedstock in combination with the solution of mineral acid, water-miscible solvent, and metal halide, and can be affected, for example, by the specific feedstock used and the particle size. "Solids" refers to all components in the mixture that remain insoluble. The feedstock concentration can be maximized to the extent possible to minimize the volume of the contacting vessel and to make the process more economical. From a practical viewpoint, high ratios of the weight of feedstock to the weight of water plus water-miscible solvent plus metal halide may be limited by the ability to provide sufficient mixing, or intimate contact, for contacting to occur at a practical rate.

The lignocellulosic feedstock contains glucan and xylan. The source of the lignocellulosic feedstock is not critical, and the biomass can be from any source. Biomass can be derived from a single source, or biomass can comprise a mixture derived from more than one source; for example, biomass can comprise a mixture of corn cobs and corn stover, or a mixture of grass and leaves. Biomass sources include, for example, bioenergy crops, agricultural residues, municipal solid waste, industrial solid waste, sludge from paper manufacture, yard waste, wood and forestry waste or a combination thereof. Examples of biomass include: corn grain, corn cobs, crop residues such as corn husks, corn stover, grasses, wheat, wheat straw, barley, barley straw, hay, rice straw, switchgrass, sugar cane bagasse, sorghum, soy, components obtained from milling of grains, trees, branches, roots, leaves, wood chips, sawdust, shrubs and bushes, vegetables, fruits, flowers, and animal manure, and combinations thereof. Biomass that is useful for the processes disclosed herein can include biomass that has a relatively high carbohydrate value, is relatively dense, and/or is relatively easy to collect, transport, store and/or handle. In some preferred embodiments, the biomass is selected from corn cobs, wheat straw, sawdust, and sugar cane bagasse.

Lignocellulosic feedstock can be used directly as obtained from the source, or energy can be applied to the biomass to reduce the size, increase the exposed surface area, and/or increase the availability of lignin, cellulose, hemicellulose, and/or oligosaccharides present in the biomass to the aqueous solution in the reaction mixture. Suitable methods for applying energy for reducing the size, increasing the exposed surface area, and/or increasing the availability of lignin, cellulose, hemicellulose, and/or oligosaccharides present in lignocellulosic feedstock include milling, crushing, grinding, shredding, chopping, disc refining, ultrasound, and microwave. Application of energy can be carried out before and/or during contacting with the aqueous solution. Lignocellulosic feedstock can be used directly as obtained from the source or can be dried to reduce the amount of moisture contained therein. Ligonocellulosic feed stock can also be subjected to chemical pretreatments to alter the composition and the structure of the biomass. For example, biomass feedstock can be pretreated with ammonia, caustic, or organosol extraction methods to remove partially the lignin in the biomass, thereby enriching the carbohydrate content.

Hemicellulosic materials and $C_5$ sugar monomers such as xylose and arabinose and their oligomers and polymers can be used directly as feedstocks. As used herein, the term "oligomers" refers to molecules containing 20 or fewer monomer units. Hemicellulose is an amorphous polymer that consists of short, highly branched chains of five different sugars, as defined further hereinabove.

Reaction Conditions

The feedstock is contacted with an aqueous solution comprising metal halide, water-miscible organic solvent, mineral acid, and water.

The metal halide is present in the reaction mixture at about 0.1 to about 2 weight percent based on the weight of the reaction mixture. In some embodiments, the metal halide is present in the reaction mixture at a weight percentage between and optionally including any two of the following values: 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, and 2.0 weight percent. In some embodiments, the metal halide is a metal chloride, a metal bromide, or a metal iodide. In some embodiments, the metal halide is an alkali halide, an alkaline earth halide, or a transition metal halide. Mixtures of metal halides can also be used. In some embodiments, the metal halide is NaCl, NaI, NaBr, CaCl$_2$, CaBr$_2$, NiCl$_2$, NiBr$_2$, or a mixture of any of these. In some embodiments, the metal halide is NaCl. It is desirable not to exceed an amount of metal halide at which the aqueous solution becomes biphasic.

The mineral acid is present in the reaction mixture at about 0.5 to about 4 weight percent based on the weight of the reaction mixture. In some embodiments, the mineral acid is present in the reaction mixture at a weight percentage between and optionally including any two of the following values: 0.5, 1.0, 1.5, 2.0, 2.5, 3.0, 3.5, and 4.0 weight percent. In some embodiments, the mineral acid is sulfuric acid (H$_2$SO$_4$), hydrochloric acid (HCl), or phosphoric acid (H$_3$PO$_4$). Mineral acid mixtures can also be used.

The water-miscible organic solvent is present in the reaction mixture at about 10 weight percent and about 80 weight percent based on the weight of the reaction mixture. In some embodiments, the water-miscible organic solvent is present in the reaction mixture at about 50 weight percent and about 80 weight percent. In some embodiments, the water-miscible organic solvent is present in the reaction mixture at about 70 weight percent and about 80 weight percent. In some embodiments, the water-miscible organic solvent is present in the reaction mixture at a weight percentage between and optionally including any two of the following values: 10, 15, 20, 25, 30, 35, 40, 45, 50, 55, 60, 65, 70, 75, and 80 weight percent. In some embodiments, the water-miscible organic solvent is an ether. Examples of suitable ethers include: tetrahydrofuran ("THF"), dioxane, 2-methoxy-methylethoxy-propanol, and dimethyl ether. Mixtures of ethers can also be used. In some embodiments, the ether is THF.

The reaction mixture is heated at a reaction temperature in the range from about 140° C. to about 190° C. for a period of time of time ranging from about 1 minute to about 10 hours. In some embodiments, the temperature is between and optionally including any two of the following values: 140, 145, 150, 155, 160, 165, 170, 175, 180, 185, and 190° C. In some embodiments, the reaction mixture is heated at a reaction temperature in the range from about 155° C. to about 165° C. The appropriate temperature depends on the specific situation (e.g., type of feedstock, feedstock particle size, component concentrations) and is readily determined by one of ordinary skill in the art.

In some embodiments, the reaction mixture is heated for a period of time between and optionally including any two of the following values: 1 min, 5 min, 10 min, 0.25 h, 0.33 h, 0.42 h, 0.5 h, 0.75 h, 1 h, 2 h, 3 h, 4 h, 5 h, 6 h, 7 h, 8 h, 9 h, and 10 h. In some embodiments, the reaction mixture is heated for about 5 minutes to about 4 hours. The amount of time depends on reaction conditions such as temperature, type of feedstock, feedstock particle size, component concentrations; and is readily determined by one of ordinary skill in the art.

The processes disclosed herein can be performed in any suitable vessel, such as a batch reactor a continuous reactor. The suitable vessel may be equipped with a means, such as impellers, for agitating the reaction mixture. Reactor design is discussed, for example, by Lin, K.-H., and Van Ness, H. C. (in Perry, R. H. and Chilton, C. H. (eds.), *Chemical Engineer's Handbook*, 5th Edition (1973) Chapter 4, McGraw-Hill, N.Y.). The contacting step may be carried out as a batch process, or as a continuous process.

After the reaction mixture has been heated for the appropriate period of time as recited above, the furfural thereby produced is recovered by an appropriate method known in the art, such as, for example, adsorption by resins, separation by molecular sieves, or pervaporation. In one embodiment, distillation is used to recover the furfural from the reaction mixture.

EXAMPLES

The methods disclosed herein are illustrated in the following examples. From the above discussion and these examples, one skilled in the art can ascertain the essential characteristics of this invention, and without departing from the spirit and scope thereof, can make various changes and modifications of the invention to adapt it to various uses and conditions.

Materials

The following materials were used in the examples. All commercial reagents were used as received. Sulfuric acid, tetrahydrofuran, sodium chloride, sodium bromide, calcium chloride, calcium bromide, nickel(II) chloride, nickel(II) bromide, manganese (II) chloride, magnesium bromide, hydrochloric acid, 1,4-dioxane, and dimethyl sulfoxide (DMSO) were obtained from Sigma-Aldrich (St. Louis, Mo.). 2-methoxy-methylethoxy-propanol was obtained from Arch Chemicals, Inc. (Norwalk, Conn.). Deionized water was used unless otherwise noted. The sea water was collected from Wildwood, N.J., USA.

Corn cob particles (+10/−14 mesh) were purchased from Independence Corn Byproducts Co. (Independence, Iowa). Wheat straw, sorghum and sugarcane bagasse were obtained from the National Institute of Standards & Technology (Gaithersburg, Md.). Both were −20/+74 mesh. Poplar sawdust was collected from a local sawmill. All biomass feedstocks were used as received.

The carbohydrate composition of the biomasses was determined according to the NREL method NREL/TP-510-42618. The moisture content of the corn cob and poplar sawdust was determined by weighing the biomass before and after drying in a vacuum oven overnight at 120° C. The moisture content of the bagasse and wheat straw was measured according to NREL/TP-510-42621. The initial carbohydrate compositions of the feedstocks are reported in Table 1. The pentosan content is reported as the sum of the xylan and arabinan components. Pentose concentrations are reported as the sum of xylose and arabinose.

TABLE 1

Carbohydrate Composition of Lignocellulosic Biomass Feedstocks Used

| Feedstock | Composition (weight percent) | | | |
|---|---|---|---|---|
| | Glucan | Xylan | Arabinan | Pentosans |
| bagasse | 36.14 | 24.03 | 2.35 | 26.38 |
| corn cob | 37.70 | 29.73 | 4.26 | 33.99 |
| corn stover | 37.75 | 22.18 | 3.32 | 25.49 |
| sorghum | 38.83 | 20.13 | 3.19 | 23.32 |
| switchgrass | 37.90 | 26.89 | 3.17 | 30.06 |
| wheat straw | 40.50 | 22.47 | 3.14 | 25.62 |
| xylan | 2.70 | 78.50 | 0.50 | 79.00 |
| yellow poplar | 43.50 | 19.35 | 0.58 | 19.93 |
| bamboo | 40.08 | 21.60 | 1.00 | 22.60 |

The following abbreviations are used: "Comp Ex" means Comparative Example, "DMSO" means dimethylsulfoxide, g" means gram(s), "HPLC" means high pressure liquid chromatography, "HMF" means 5-hydroxymethyl furfural, "M" means molar, "mm" means millimeter(s), "mg" means milligram(s), "min" means minute(s), "mL" means milliliter(s), "N" means normal, "ND" means not determined, "rep" means repeated, "RPM" means revolutions per minute, "Temp" means temperature, "THF" means tetrahydrofuran, "weight percent" means weight percent(age), "µL" means microliter(s), and "µm" means micrometer(s).

General Procedure

Preparation of furfural from biomass feedstock was conducted in batch mode using the procedure disclosed here. Batch reactions were performed in a 160 mL mini bench top autoclave reactor (model 4561, Parr Instrument Co., Moline, Ill.) with all internal wetted parts constructed from ZR702 zirconium. External fittings were constructed with 316 stainless steel. Heat was supplied by an external electrical mantle. The reaction mixture was stirred at 300 RPM. Unless otherwise specified, the solvent mixture for furfural reactions consisted of water—0.15 M sulfuric acid, or water—1% metal halide—015 M sulfuric acid, or water—0.15 M sulfuric acid—organic solvent or water—1% metal halides—0.15 M sulfuric acid—organic solvent. The metal halide and the acid concentration were based on the weight of the total reaction mixture. In a typical experiment, biomass was combined with the chosen solvent mixture and thoroughly mixed. The reactor was sealed and purged with nitrogen prior to heating to the reaction temperature over a short period (typically, about 13 minutes). The reaction mixture was maintained at this temperature for a specified duration. At the conclusion of the reaction, the vessel was submerged in an ice bath to rapidly quench the mixture to room temperature (under 25° C.). A known quantity of DMSO, to be used as HPLC internal standard, was added to the reaction mixture and thoroughly mixed. The contents of the reactor were transferred to a glass bottle. The reaction mixture was then handled as described below.

Analysis of Reaction Mixture

The cooled reaction mixture was diluted by the same volume of reaction solvent used in the reaction. Prior to dilution, enough DMSO was added to this solvent to give a final concentration of 5 mg DMSO/gram of the reaction mixture. The diluted reaction mixture is thoroughly mixed. For reaction containing only water, the sample was filtered through a 0.2 µm filter. For reactions containing aqueous organic solvent, the reaction liquid sample was further diluted with twice the sample volume of water to precipitate any water insoluble matter and the diluted sample solution was filtered through a 0.2 µm filter. The soluble products in the reaction mixture, namely glucose, xylose, arabinose, acetic acid, formic acid, levulinic acid, 5-hydroxymethyl furfural and furfural were measured by HPLC system (Waters Alliance Model, Milford, Mass., USA) containing Water 2695 Seperation Module and 2414 RI Detector and by using Bio-Rad HPX-87H column (Bio-Rad Laboratories, Hercules, Calif., USA) fitted with appropriate guard columns. The eluant used was 0.01 N aqueous sulfuric acid at a flow rate of 0.6 mL/minute. The column, guard column and RI Detector were held at 50° C. and 10-50 µL injections were used, dependent on concentration and detector limits. Individual sample run times were 60 minutes. After the run, concentrations in the sample were determined from standard curves created from authentic samples for each of the compounds.

Furfural and hydroxymethylfurfural yields reported below are based on the respective glucan and xylan plus arabinan compositions in the unreacted lignocellulosic biomass. For comparative analysis of the effect of reaction solvent and additive salts, furfural produced in the reaction mixture is expressed in millimoles produced per gram of dry biomass used in the reaction.

Comparative Examples A, B

Furfural Synthesis by Standard Acid Treatment of Corn Cob

ICBP Corn Cob (18.9 g, 1-2 mm, 92.5% dry matter) at 25% solid loading was placed in the reactor containing 0.15 M aqueous sulfuric acid (Comparative Example A) or 0.15 M aqueous hydrochloric acid solution (Comparative Example B) (51.1 g) and gradually heated to 160° C. over a period of 13 min and then maintained at this temperature for 30 min as described in the general procedure. At the end of the reaction, the reaction mixture was diluted with water (103.2 g) containing DMSO (1.33 g) and thoroughly mixed. A sample of this reaction mixture was analyzed as described above for xylose and furfural content. The reaction was repeated under identical conditions to validate the reproducibility of data. Results are presented in Table 2. A mixture of furfural, xylose and arabinose was obtained, indicating incomplete conversion of hemicellulose to the desired product furfural.

TABLE 2

| Reaction- | Solvent System | NaCl Loading | % Yield | | | | | |
|---|---|---|---|---|---|---|---|---|
| | | | Furfural | HMF | Xylose | Arabinose | Formic Acid | Total |
| Comp Ex A | 0.15M H$_2$SO$_4$ | no NaCl | 24 | 1 | 34 | 6 | 3 | 69 |
| Comp Ex A (rep) | | no NaCl | 24 | 1 | 34 | 6 | 3 | 69 |
| Comp Ex B | 0.15M HCl | no NaCl | 28 | 1 | 37 | 8 | 11 | 85 |
| Comp Ex B (rep) | | no NaCl | 28 | 1 | 32 | 7 | 10 | 78 |

Example 1

Furfural Synthesis from Corn Cob at High Solid Loading (25%)

ICBP Corn Cob (18.9 g, 1-2 mm, 92.5% dry matter) was placed in the reactor containing sulfuric acid (1.07 g) plus one of the following solvent systems to form a reaction mixture:

| Run | Reaction Solvent System |
|---|---|
| 1A | Solvent A: water (8.02 g) plus THF (42.0 g), |
| 1B | Solvent B: water (7.31 g) plus THF (42.0 g) plus sodium chloride (0.7 g) |
| 1C | Water (49.3 g) plus sodium chloride (0.7 g) |

Each reaction mixture was gradually heated to 160° C. over a period of 13 min and then maintained at this temperature for 30 min as described in the general procedure. At the end of the reaction, each reaction mixture was diluted as indicated below and thoroughly mixed.

| Run | Dilution Solvent |
|---|---|
| 1A | Water (8.02 g) plus THF (42.0 g), |
| 1B | Water (7.31 g) plus THF (42.0 g) plus sodium chloride (0.7 g) |
| 1C | Water (98.8 g) containing DMSO (1.4 g) |

A sample of each diluted reaction mixture was analyzed as described above for xylose, arabinose, formic acid and furfural content Results are reported in Table 3. The reactions were run in duplicate for water/sodium chloride and for solvent A and in triplicate for solvent B. For comparison, the results from Comparative Example A (using neither THF nor sodium chloride) are included as well. The results show that addition of THF accelerated the conversion of xylose to furfural, whereas the addition of THF and sodium chloride to the reaction mixture both accelerated the conversion of xylose to furfural and increased overall yield of furfural from corn cob.

TABLE 3

| | | Salt | % Yield | | |
|---|---|---|---|---|---|
| Run | Solvents | Loading | Furfural | Xylose | Arabinose |
| Comp Ex A | water | no salt | 24 | 34 | 6 |
| Comp Ex A(rep) | water | no salt | 24 | 34 | 6 |
| 1C | water | 1% NaCl | 29 | 26 | 7 |
| 1C (rep) | water | 1% NaCl | 30 | 22 | 6 |
| 1A | Solvent A | no salt | 52 | 2 | 3 |
| 1A (rep) | Solvent A | no salt | 53 | 2 | 3 |
| 1B | Solvent B | 1% NaCl | 86 | 3 | 3 |
| 1B (rep) | Solvent B | 1% NaCl | 83 | 3 | 2 |
| 1B (rep) | Solvent B | 1% NaCl | 87 | 3 | 3 |

Reaction conditions: 25% cob + 0.15M $H_2SO_4$, 160° C., 30 min

In FIG. 1, furfural yield from corn cob at 25% dry mass loading using 0.15 M sulfuric acid dehydration in water (duplicate) is compared with that for water-THF (solvent system A) and water-THF-sodium chloride (solvent system B). Addition of solvent system A accelerates the conversion of xylose to furfural, whereas the addition of solvent system B accelerates the xylose conversion and enhances the yield of furfural.

FIG. 1 indicates formation of combined xylose/furfural yield from corn cob when the reaction is conducted in water, water-THF and water-THF containing 1% sodium chloride. These reactions were done in duplicates to confirm the reproducibility of the reaction. In water alone, the yield consisted of both nearly equal amounts of xylose and furfural, indicating slow conversion of xylose to furfural. On the other hand, when THF is added to the reaction, there was complete conversion of xylose to furfural, but the total xylose/furfural yield remained the same. Unexpectedly, addition of sodium chloride together with THF increased both the conversion of xylose and total yield to a substantially higher range than in previous methods.

Example 2

Furfural Synthesis from Corn Cob at Moderate Solids Loading (10%)

ICBP Corn Cob (7.6 g, 1-2 mm, 92.5% dry matter) was placed in the reactor containing a solution of sulfuric acid (1.07 g) plus one of the following solvent systems to form a reaction mixture:

| Run | Reaction Solvent System |
|---|---|
| 2A | Water (61.4 g) |
| 2B | Water (60.7 g) plus sodium chloride (0.70 g) |
| 2C | Water (10.0 g) plus THF (51.4 g); |
| 2D | Water (9.8 g) plus THF (50.8 g) plus sodium chloride (0.7 g) |

Each reaction mixture was gradually heated to 160° C. over a period of 13 min and then maintained at this temperature for 30 min as described in the general procedure. At the end of the reaction, each reaction mixture was diluted as indicated below and thoroughly mixed.

| Run | Dilution Solvent |
|---|---|
| 2A | Water (69.5 g) containing DMSO (1.3 g) |
| 2B | Water (69.5 g) containing DMSO (1.3 g) |
| 2C | Water (13.8 g) plus THF (58.8 g) containing DMSO (1.1 g) |
| 2D | Water (13.8 g) plus THF (58.8 g) containing DMSO (1.1 g) |

A sample of each diluted reaction mixture was analyzed as described above for xylose, arabinose, formic acid and furfural content. Results are reported in Table 4. The reaction was repeated under identical conditions to validate the reproducibility of data. As can be seen from Table 4, addition of THF to the reaction mixture accelerated the conversion of xylose to furfural, whereas the addition of THF and sodium chloride both accelerated the xylose conversion and increased the yield of furfural essentially to the theoretical limit.

TABLE 4

| Run | Solvent System | NaCl Loading | % Yield | | | |
|---|---|---|---|---|---|---|
| | | | Furfural | HMF | Xylose | Arabinose |
| 2A | 100% $H_2O$ | 0% | 28 | 1 | 43 | 6 |
| 2A (rep) | | 0% | 29 | 1 | 43 | 6 |
| 2B | | 1% | 32 | 1 | 36 | 5 |
| 2B (rep) | | 1% | 33 | 1 | 36 | 7 |
| 2C | THF-$H_2O$ | 0% | 63 | 17 | 0 | 7 |
| 2C (rep) | | 0% | 63 | 16 | 2 | 5 |
| 2D | THF-$H_2O$ | 1% | 100 | 40 | 1 | 3 |
| 2D (rep) | | 1% | 99 | 39 | 3 | 3 |

Example 3

Dependence of Furfural Yield from Corn Cob (25% Dry Mass Loading) on Sodium Chloride Content To gauge the effect of sodium chloride content on the outcome of furfural yield, the amount of sodium chloride was increased to 1.5% of the reaction mass while keeping the THF at 60% of the reaction mass. The reaction was conducted as described in Example 1. Results are presented in Table 5, along with those for Run 1B. The increase in sodium chloride in Run 3 versus Run 1B resulted in moderate yield improvement. Furthermore, less formic acid was also formed at the higher salt concentration, indicating less decomposition of the product furfural. Runs with still higher levels of sodium chloride were not conducted, since when NaCl concentration was greater than 2%, the THF-water solution became biphasic.

TABLE 5

| Run | Salt Loading | Solvents* | % Yield | | | Formic Acid |
|---|---|---|---|---|---|---|
| | | | Furfural | Xylose | Arabinose | |
| 1B | 1% NaCl | THF-water | 86 | 3 | 3 | 5 |
| 1B (rep) | | THF-water | 83 | 3 | 2 | 4 |
| 1B (rep) | | THF-water | 87 | 3 | 3 | 6 |
| 3 | 1.5% NaCl | THF-water | 91 | 3 | 2 | 2 |
| 3 (rep) | | THF-water | 94 | 2 | 1 | 0 |

25% corn cob loading.
*THF is 60% of reaction mass.

Example 4

Dependence of Furfural Yield from Corn Cob (10% Dry Mass Loading) on THF Content To gauge the effect of THF content on furfural yield, THF as a reaction solvent was varied from 0% to 87% of the reaction mass while keeping the sodium chloride content at 1%. The reaction was conducted as described in Example 2. Results are presented in Table 6. The conversion of xylose to furfural dramatically increased with 50% or more of THF. Also, the formation of formic acid decreased unexpectedly resulting in increased furfural yield. In the case of run 4J, no water was added, so the hydrolysis of xylan and its conversion to furfural was slow and not complete in 30 min.

TABLE 6

| Run | Reaction Conditions | THF as % of reaction mass | % Yield | | | |
|---|---|---|---|---|---|---|
| | | | Furfural | Xylose | Arabinose | Formic Acid |
| 4A | 10% cob + | 0 | 35 | 39 | 6 | 11 |
| 4B | 0.15M | 10% | 41 | 30 | 10 | 23 |
| 4C | H₂SO₄ + | 25% | 45 | 34 | 9 | 17 |
| 4D | 1% NaCl, | 40% | 58 | 19 | 8 | 23 |
| 4E | 160° C., | 45% | 63 | 14 | 7 | 13 |
| 4F | 30 min | 50% | 78 | 4 | 0 | 8 |
| 4G | | 60% | 78 | 3 | 4 | 0 |
| 4H | | 80% | 83 | 2 | 2 | 2 |
| 4I | | 80% | 82 | 2 | 2 | 2 |
| 4J | | 87% | 61 | 1 | 3 | 6 |

Example 5

Preparation of Furfural from Corn Stover (10% Solids Loading)

Corn stover (5.6 g, 1-2 mm, 89.5% dry matter) was placed in the reactor containing a solution of sulfuric acid (0.77 g) in a solvent system as indicated below to form a reaction mixture:

| Run | Reaction solvent system |
|---|---|
| 5A | Water (43.7 g) |
| 5B | Water (6.9 g) plus THF (36.7 g) |
| 5C | Water (6.9 g) plus THF (36.3 g) plus sodium chloride (0.5 g) |

Each reaction mixture was gradually heated to 160° C. over a period of 13 min and then maintained at this temperature for 30 min as described in the general procedure. At the end of the reaction, the reaction mixture was processed and analyzed as described in Example 1. Results are presented in Table 7. As seen in the case of corn cob, THF addition alone (5B) led to higher xylose conversion versus 5A, while higher furfural yield was observed with THF-NaCl combination (5C).

TABLE 7

| Run | Solvent System | NaCl Loading | % Yield | | |
|---|---|---|---|---|---|
| | | | Furfural | Xylose | Arabinose |
| 5A | H₂O, no THF | 0 | 29 | 42 | 8 |
| 5A (rep) | | 0 | 27 | 42 | 8 |
| 5B | 83/17 THF/H₂O | 0 | 62 | 3 | 5 |
| 5B (rep) | | 0 | 64 | 1 | 2 |
| 5C | | 1% NaCl | 95 | 2 | 4 |
| 5C (rep) | | 1% NaCl | 92 | 1 | 2 |

10% corn stover + 0.15M H₂SO₄, 160° C., 30 min

Example 6

Preparation of Furfural from Bagasse at 10% Solids Loading

Bagasse (5.8 g, 1-2 mm, 86.2% dry matter) was placed in the reactor containing a solution of sulfuric acid (0.77 g) in a solvent system as indicated below to form a reaction mixture:

| Run | Reaction solvent system |
|---|---|
| 6A | Water (43.4 g) |
| 6B | Water (6.9 g) plus THF (36.7 g) |
| 6C | Water (6.6 g) plus THF (36.3 g) plus sodium chloride (0.5 g) |

Each reaction mixture was gradually heated to 160° C. over a period of 13 min and then maintained at this temperature for 30 min as described in the general procedure. At the end of the reaction, each reaction mixture was processed and analyzed as described in Example 2. Results are presented in Table 8. THF addition alone resulted in higher xylose conversion to furfural and the THF-NaCl combination increased yield.

TABLE 8

| Run | Solvent System | NaCl Loading | % Yield Furfural | HMF | Xylose | Arabinose | Formic Acid |
|---|---|---|---|---|---|---|---|
| 6A | H$_2$O, | 0 | 34 | 1 | 36 | 4 | 2 |
| 6A (rep) | no THF | 0 | 33 | 1 | 34 | 4 | 2 |
| 6B | 83/17 | 0 | 60 | 13 | 0 | 2 | 0 |
| 6B (rep) | THF/ H$_2$O | 0 | 61 | 16 | 0 | 8 | 0 |
| 6C | | 1% NaCl | 103 | 40 | 0 | 2 | 0 |
| 6C (rep) | | 1% NaCl | 106 | 39 | 0 | 4 | 0 |

10% bagasse + 0.15M H$_2$SO$_4$, 160° C., 30 min

Example 7

Preparation of Furfural from Wheat Straw at 10% Solids Loading

Wheat straw (5.18 g, 1-2 mm, 86.2% dry matter) was placed in the reactor containing a solution of sulfuric acid (0.77 g) in a solvent system as indicated below:

| Run | Reaction solvent system |
|---|---|
| 7A | Water (44.05 g) |
| 7B | Water (6.82 g) plus THF (36.71 g) |
| 7C | Water (6.73 g) plus THF (36.30 g) plus sodium chloride (0.5 g) |

Each reaction mixture was gradually heated to 160° C. over a period of 13 min and then maintained at this temperature for 30 min as described in the general procedure. At the end of the reaction, the reaction mixture was processed and analyzed as described in Example 2. Results are presented in Table 9. THF addition alone resulted in higher xylose conversion to furfural and the THF-NaCl combination increased yield.

TABLE 9

| Run- | Solvent System | NaCl Loading | % Yield Furfural | HMF | Xylose | Arabinose | Formic Acid |
|---|---|---|---|---|---|---|---|
| 7A | H$_2$O, | 0 | 26 | 1 | 43 | 7 | 2 |
| 7A (rep) | no THF | 0 | 26 | 1 | 43 | 7 | 3 |
| 7B | 83/17 | 0 | 59 | 15 | 3 | 6 | 3 |
| 7B (rep) | THF/ H$_2$O | 0 | 58 | 14 | 0 | 2 | 0 |
| 7C | | 1% NaCl | 104 | 24 | 1 | 3 | 5 |
| 7C (rep) | | 1% NaCl | 100 | 25 | 0 | 0 | 0 |

10% wheat straw + 0.15M H$_2$SO$_4$, 160° C., 30 min

Example 8

Preparation of Furfural from Sorghum at 10% Solids Loading

Corn Sorghum (5.43 g, 1-2 mm, 92.1% dry matter) was placed in the reactor containing a solution of sulfuric acid (0.77 g) in a solvent system as indicated below:

| Run | Reaction solvent system |
|---|---|
| 8A | Water (43.80 g) |
| 8B | Water (7.1 g) plus THF (36.7 g) |
| 8C | Water (7.0 g) plus THF (36.3 g) plus sodium chloride (0.5 g) |

Each reaction mixture was gradually heated to 160° C. over a period of 13 min and then maintained at this temperature for 30 min as described in the general procedure. At the end of the reaction, the reaction mixture was processed and analyzed as described in Example 1. Results are presented in Table 10.

TABLE 10

| Run | Solvent System | NaCl Loading | % Yield Furfural | HMF | Xylose | Arabinose | Formic Acid |
|---|---|---|---|---|---|---|---|
| 8A | H$_2$O, no | 0 | 22 | 2 | 50 | 10 | 7 |
| 8A (rep) | THF | 0 | 20 | 2 | 49 | 13 | 5 |
| 8B | 83/17 | 0 | 61 | 18 | 1 | 0 | 7 |
| 8B (rep) | THF/ H$_2$O | 0 | 67 | 20 | 0 | 2 | 10 |
| 8C | | 1% NaCl | 101 | 31 | 1 | 0 | 5 |
| 8C (rep) | | 1% NaCl | 102 | 31 | 1 | 0 | 4 |

10% *sorghum* + 0.15M H$_2$SO$_4$, 160° C., 30 min

Example 9

Preparation of Furfural from Switchgrass at 10% Solids Loading

Switchgrass (5.45 g, 1-2 mm, 91.7% dry matter) was placed in the reactor containing a solution of sulfuric acid (0.77 g) in a solvent system as indicated below to form a reaction mixture:

| Run | Reaction solvent system |
|---|---|
| 9A | Water (43.8 g) |
| 9B | Water (7.1 g) plus THF (36.7 g) |
| 9C | Water (7.0 g) plus THF (36.3 g) plus sodium chloride (0.5 g) |

Each reaction mixture was gradually heated to 160° C. over a period of 13 min and then maintained at this temperature for 30 min as described in the general procedure. At the end of the reaction, the reaction mixture was processed and analyzed as described in Example 2. Results are presented in Table 11. THF addition alone resulted in higher xylose conversion to furfural and the THF-NaCl combination produced higher yield.

TABLE 11

| Run | Solvent System | NaCl Loading | % Yield Furfural | HMF | Xylose | Arabinose | Formic Acid |
|---|---|---|---|---|---|---|---|
| 9A | H$_2$O, | 0 | 34 | 1 | 35 | 8 | 4 |
| 9A (rep) | no THF | 0 | 31 | 1 | 39 | 8 | 3 |
| 9B | 83/17 | 0 | 58 | 13 | 1 | 4 | 2 |

TABLE 11-continued

| Run | Solvent System | NaCl Loading | % Yield | | | | |
|---|---|---|---|---|---|---|---|
| | | | Furfural | HMF | Xylose | Arabinose | Formic Acid |
| 9B (rep) | THF/H$_2$O | 0 | 59 | 14 | 0 | 2 | 0 |
| 9C | | 1% NaCl | 110 | 37 | 0 | 10 | 11 |
| 9C (rep) | | 1% NaCl | 102 | 30 | 0 | 6 | 7 |

10% switchgrass + 0.15M H$_2$SO$_4$, 160° C., 30 min

| Run | Reaction solvent system |
|---|---|
| 10A | Water (43.9 g) |
| 10B | Water (7.2 g) plus THF (36.7 g) |
| 10C | Water (7.1 g) plus THF (36.3 g) plus sodium chloride (0.5 g) |

Each reaction mixture was gradually heated to 160° C. over a period of 13 min and then maintained at this temperature for 30 min as described in the general procedure. At the end of the reaction, the reaction mixture was processed and analyzed for xylose, arabinose, formic acid, HMF, and furfural content as described in Example 2. Results are presented in Table 12. THF addition alone resulted in higher xylose conversion to furfural and the THF-NaCl combination produced higher yield.

TABLE 12

| Run | Solvent System | NaCl Loading | % Yield | | | | | |
|---|---|---|---|---|---|---|---|---|
| | | | Furfural | HMF | Xylose | Arabinose | Formic Acid | Total |
| 10A | H$_2$O only, | 0 | 33 | 21 | 41 | 0 | 3 | 98 |
| 10A (rep) | no THF | 0 | 31 | 21 | 46 | 0 | 3 | 101 |
| 10B | 83/17 | 0 | 59 | 0 | 0 | 2 | 2 | 63 |
| 10B (rep) | THF/H$_2$O | 0 | 59 | 0 | 0 | 1 | 3 | 63 |
| 10C | | 1% NaCl | 80 | 0 | 0 | 3 | 2 | 85 |
| 10C (rep) | | 1% NaCl | 76 | 0 | 0 | 3 | 3 | 82 |

10% birchwood xylans + 0.15M H$_2$SO$_4$, 160° C., 30 min

Example 10

Preparation of Furfural from pH-Adjusted Birchwood Xylans at Moderate Solids Loading (10%)

Birchwood xylan when suspended in water exhibited high pH due to residual base in the commercial product. Therefore, a pH adjustment step was carried out prior to it being used as a starting material for furfural production. To adjust the pH, moist birchwood xylan (87.61 g, Sigma Chemical Company, St. Louis, Mo., USA) was suspended in H$_2$O (~1 L) and stirred. To this, a dilute H$_2$SO$_4$ solution (112.09 g of 4.8% H$_2$SO$_4$ solution) was added drop-wise causing the pH to drop from 5.70 to 2.01. Filtration of this mixture was attempted, but proved to be very slow. Instead, the mixture was then divided into equal portions and centrifuged (8000 RPM, 20 min), causing pellets to form. The mother liquors were decanted off and fresh water was added to the pellets (~1 L total). These mixtures were shaken to disperse the pellets and then centrifuged (8000 RPM, 20 min). The wash liquid was decanted off the pellets and the pellets were transferred from the centrifuge bottles to aluminum trays and placed in a nitrogen oven set at 45° C. for 2.5 days causing hard brown chunks to form. The solids were collected (97.59 g) and a sample was taken to determine moisture content: 94.0%, giving 91.73 g dry solids.

The pH-adjusted Birchwood xylan (5.32 g, 1-5 mm, 94.0% dry matter) was placed in the reactor containing a solution of sulfuric acid (0.77 g) in a solvent system as indicated below to form a reaction mixture:

Example 11

Preparation of Furfural from Yellow Poplar at High Solids Loading (25%)

Yellow poplar (15.45 g, 1-2 mm, 80.9% dry matter) was placed in the reactor containing a solution of sulfuric acid (0.77 g) in a solvent system as indicated below to form a reaction mixture:

| Run | Reaction solvent system |
|---|---|
| 11A | Water (33.8 g) |
| 11B | Water (3.3 g) plus THF (30.5 g) |
| 11C | Water (3.2 g) plus THF (30.1 g) plus sodium chloride (0.5 g) |

Each reaction mixture was gradually heated to 160° C. over a period of 13 min and then maintained at this temperature for 30 min as described in the general procedure. At the end of the reaction, each reaction mixture was processed as described in Example 2. A sample of each reaction mixture was analyzed as described above for xylose, arabinose, formic acid, HMF, and furfural content. Results are presented in Table 13. THF addition alone resulted in higher xylose conversion to furfural and the THF-NaCl combination produced higher yield.

TABLE 13

| Run- | Feedstock Loading | Solvent System | NaCl Loading | % Yield | | | | | |
|---|---|---|---|---|---|---|---|---|---|
| | | | | Furfural | HMF | Xylose | Arabinose | Formic Acid | Total |
| 11A | 25% yellow poplar | H₂O only, no THF | 0 | 25 | 1 | 20 | 3 | 2 | 50 |
| 11B | 25% yellow poplar | 83/17 THF/H₂O | 0 | 30 | 7 | 4 | 6 | 6 | 53 |
| 11C | 25% yellow poplar | 83/17 THF/H₂O | 1% NaCl | 68 | 17 | 0 | 3 | 4 | 92 |

25% yellow poplar + 0.15M H₂SO₄, 160° C., 30 min

Example 12

Preparation of Furfural from Bamboo (10% Solids Loading)

Bamboo (6.82 g, 1 mm, 73.3% dry matter) was placed in the reactor containing a solution of sulfuric acid (0.77 g) in a solvent system as indicated below to form a reaction mixture:

| Run | Reaction solvent system |
|---|---|
| 12A | Water (42.4 g) |
| 12B | Water (5.7 g) plus THF (36.7 g) |
| 12C | Water (5.6 g) plus THF (36.3 g) plus sodium chloride (0.50 g) |

Each reaction mixture was gradually heated to 160° C. over a period of 13 min and then maintained at this temperature for 30 min as described in the general procedure. At the end of the reaction, the reaction mixture was processed as described in Example 2. A sample of each reaction mixture was analyzed as described above for xylose, arabinose, formic acid, HMF and furfural content. Results are presented in Table 14. THF addition alone resulted in higher xylose conversion to furfural and the THF-NaCl combination produced higher yield.

TABLE 14

| Rxn | Conditions | | % Yield | | | | | |
|---|---|---|---|---|---|---|---|---|
| | | | Furfural | HMF | Xylose | Arabinose | Formic Acid | Total |
| 12A | H₂O only, no THF | no NaCl | 35 | 1 | 50 | 5 | 5 | 96 |
| 12A (rep) | H₂O only, no THF | no NaCl | 36 | 1 | 44 | 4 | 3 | 88 |
| 12B | 83/17 THF/H₂O | no NaCl | 66 | 12 | 1 | 5 | 3 | 87 |
| 12B (rep) | THF/H₂O | no NaCl | 64 | 11 | 2 | 6 | 4 | 87 |
| 12C | | 1% NaCl | 115 | 29 | 1 | 3 | 7 | 155 |
| 12C (rep) | | 1% NaCl | 111 | 29 | 1 | 7 | 10 | 158 |

10% bamboo + 0.15M H₂SO₄, 160° C., 30 min

Example 13

Preparation of Furfural from Corn Cob at Moderate Solids Loading (10%)

ICBP Corn Cob (7.6 g, 1-2 mm, 92.5% dry matter) was converted to furfural and performance analyzed as described in Example 2 (Runs 2A, 2B), except that 1,4-dioxane was used in place of THF (Runs 14C, 14D). Results are presented in Table 15. As seen with THF, addition of 1,4-dioxane (no salt) to the reaction increases the conversion of free xylose to furfural. However, after the addition of 1% sodium chloride no further improvement in furfural yield was observed.

TABLE 15

| Exp D101845- | Solvent System | NaCl Loading | % Yield | | | | |
|---|---|---|---|---|---|---|---|
| | | | Furfural | HMF | Xylose | Arabinose | Formic Acid |
| 2A | H₂O only, no dioxane | 0 | 28 | 1 | 43 | 6 | 3 |
| 2A (rep) | | 0 | 29 | 1 | 43 | 6 | 4 |
| 2B | | 1% NaCl | 32 | 1 | 36 | 5 | 3 |
| 2B (rep) | | 1% NaCl | 33 | 1 | 36 | 7 | 3 |
| 13C | 83/17 dioxane/H₂O | 0 | 59 | 21 | 0 | 2 | 5 |
| 13C (rep) | | 0 | 59 | 20 | 0 | 2 | 6 |
| 13D | | 1% NaCl | 58 | 29 | 1 | 3 | 0 |
| 13D (rep) | | 1% NaCl | 60 | 31 | 0 | 4 | 0 |

10% corn cob + 0.15M H₂SO₄, 160° C., 30 min

Example 14

Optimization of Reaction Temperature for the High Yield Synthesis of Furfural from Corn Cob at High Solid Loading (25%) in Aqueous THF Containing 1% Sodium Chloride Corn cob (18.92 g, 1-2 mm, 92.5% dry matter) was placed in the reactor containing a solution of sulfuric acid (1.07 g) in water (7.02 g) plus THF (42.10 g) plus sodium chloride (0.70 g) to form a reaction mixture and was gradually heated to the desired reaction temperature (140, 150, 160, 170 or 180° C.) over a period of 13 min and then maintained at this temperature for 30 min as described in the general procedure. At the end of the reaction, each reaction mixture was processed as described in Example 2. A sample of each reaction mixture was analyzed as described above for xylose, arabinose, formic acid, HMF, and furfural content. Results are reported in Table 16. Based on these sets, temperature range of 150 to 170° C. appears to provide highest yield of furfural.

TABLE 16

| Run | Reaction Conditions | Temp (° C.) | % Yield | | | | | |
|---|---|---|---|---|---|---|---|---|
| | | | Furfural | HMF | Xylose | Arabinose | Formic Acid | Total |
| 14A | 25% ICBP Cob + | 140 | 87 | 7 | 5 | 3 | 4 | 106 |
| 14B | | 150 | 95 | 13 | 6 | 4 | 5 | 123 |

TABLE 16-continued

| Run | Reaction Conditions | Temp (°C.) | Fur-fural | HMF | Xy-lose | Arabi-nose | Formic Acid | Total |
|---|---|---|---|---|---|---|---|---|
| 14C | 0.15M | 150 | 93 | 12 | 6 | 5 | 4 | 120 |
| 1B | $H_2SO_4$ + | 160 | 86 | ND* | 3 | 3 | 5 | >97 |
| 14D | 1% NaCl | 170 | 94 | 37 | 0 | 3 | 2 | 136 |
| 14E | in 83/17 | 170 | 95 | 41 | 0 | 3 | 7 | 146 |
| 14F | $THF/H_2O$, 30 min | 180 | 76 | 43 | 2 | 2 | 3 | 126 |

*Not determined

Example 15

Preparation of Furfural from Corn Cob at High Solid Loading (25%) in Sea Water, in Sea Water—THF and in Sea Water—THF Containing 0.5% Sodium Chloride Corn cob (18.92 g, 1-2 mm, 92.5% dry matter) was placed in the reactor containing a solution of sulfuric acid (1.07 g) in a solvent system as indicated below to form a reaction mixture:

| Run | Reaction solvent system |
|---|---|
| 15A | Sea water (50.0 g) |
| 15B | Sea water (7.3 g) plus THF (42.7 g) |
| 15C | Sea water (7.0 g) plus THF (42.4 g) plus sodium chloride (0.35 g) |

Each reaction mixture was gradually heated to 160° C. over a period of 13 min and then maintained at this temperature for 30 min as described in the general procedure. At the end of the reaction, the reaction mixture was processed and analyzed as described in Example 2. A sample of each reaction mixture was analyzed as described above for xylose, arabinose, formic acid, HMF, and furfural content. Results are presented in Table 17 and demonstrate the suitability of sea water for these reaction in place of the expensive de-ionized water otherwise used in these Examples.

Example 16

Preparation of Furfural from Xylose at 15% Solids

Xylose (10.5 g, 98% purity) was dissolved in a solution containing $H_2SO_4$ (1.1 g, 98%) in a solvent system as indicated below to form a reaction mixture:

| Run | Reaction solvent system |
|---|---|
| 16A | Water (58.4 g) |
| 16B | Water (9.9 g) plus THF (48.5 g) |
| 16C | Water (9.8 g) plus THF (47.9 g) plus sodium chloride (0.7 g) |

Each reaction mixture was gradually heated to 160° C. over a period of 13 min and then maintained at this temperature for 30 min as described in the general procedure. At the end of the reaction, the reaction mixture was processed as described in Example 2. A sample of each reaction mixture was analyzed as described above for xylose, arabinose, formic acid, HMF, and furfural content. Results are presented in Table 18. Similar to the results observed with biomass feed stocks, addition of THF increased the xylose conversion and the addition of THF and sodium chloride further improved the furfural yield. The yield was not as high as seen in biomass conversion, indicating further solvent optimization is needed.

TABLE 18

| | | | % Yield | | | |
|---|---|---|---|---|---|---|
| Run | NaCl Loading | Solvent System | Furfural | HMF | Xylose | Formic Acid |
| 16C | 1% NaCl | 83/17 $THF/H_2O$ | 64 | 0 | 0 | 2 |
| 16B | 0 | 83/17 $THF/H_2O$ | 49 | 0 | 0 | 3 |
| 16A | 0 | $H_2O$ only, no THF | 28 | 0 | 36 | 3 |

15% xylose + 0.15M $H_2SO_4$, 160° C., 30 min

TABLE 17

| | | | | % Yield | | | | | |
|---|---|---|---|---|---|---|---|---|---|
| Run- | Reaction Conditions | Solvent System | NaCl Loading | Furfural | HMF | Xylose | Arabinose | Formic Acid | Total |
| Comp Ex A* | 25% corn cob + 0.15M $H_2SO_4$, 160° C., 30 min | $H_2O$ only, no THF | 0 | 24 | 1 | 34 | 6 | 3 | 69 |
| 1C* | | THF | 1% NaCl | 29 | 1 | 24 | 7 | 5 | 68 |
| 1A* | | 83/17 | 0 | 53 | ND | 2 | 3 | 2 | >60 |
| 1B** | | $THF/H_2O$ | 1% NaCl | 85 | ND | 3 | 2 | 4 | >94 |
| 15A | | Sea water only, no THF | 0 | 31 | 2 | 25 | 5 | 3 | 66 |
| 15B | | 83/17 | 0 | 81 | 19 | 1 | 0 | 0 | 101 |
| 15B (rep) | | THF/Sea water | 0 | 82 | 20 | 3 | 3 | 0 | 108 |
| 15C | | | 0.5% NaCl | 97 | 23 | 3 | 2 | 2 | 127 |
| 15C (rep) | | | 0.5% NaCl | 87 | 23 | 1 | 0 | 0 | 111 |

*Average of 2 runs
**Average of 3 runs

Example 17

Preparation of Furfural from Corn Cob at Moderate Solids Loading (10%) Using Various Metal Halides ICBP Corn Cob (7.6 g, 1-2 mm, 92.5% dry matter) was placed in the reactor containing a solution of sulfuric acid (0.77 g) in a solvent system in water (61.4 g); in water (60.7 g) containing metal halide (0.7 g); in water (26.4 g) containing THF (35.0 g); or in water (25.7 g) containing THF (35.0 g) and metal halide (0.7 g), to form a reaction mixture. The metal halides used were sodium, nickel and calcium bromides and chlorides. The reaction was conducted, and products processed and analyzed, as described in Example 2. Results are presented in Table 19. The addition of each metal halide to the water solvent system moderately increased both the furfural and xylose yields, and addition to the THF-water solvent system demonstrated higher selectivity to furfural over xylose.

Example 18

Comparative Synthesis of Furfural from Corn Cob at High Solid Loading (25%) in Water, in Aqueous 2,methoxy-methylethoxy-propanol and in Aqueous 2,methoxy-methylethoxy-propanol Containing 1% Sodium Chloride ICBP Corn Cob (18.92 g, 1-2 mm, 92.5% dry matter) was placed in the reactor containing a solution of sulfuric acid (1.07 g) in: water (7.3 g) plus 2-methoxy-methylethoxy-propanol (42.7 g); or water (7.2 g) plus 2-methoxy-methylethoxy-propanol (42.1 g) plus sodium chloride (0.70 g) and gradually heated to 160° C. over a period of 13 min and then maintained at this temperature for 30 min as described in the general procedure. At the end of the reaction, the reaction mixtures were processed and analyzed as described in Example 2. A sample of each reaction mixture was analyzed as described in General Methods for xylose, arabinose, formic acid, HMF and furfural content and is reported below. As can be seen from Table 20, 2-methoxy-methylethoxy-propanol behaves similar to THF in that the addition of 2-methoxy-methylethoxy-propanol increases the conversion of xylose to furfural, whereas the addition of 2-methoxy-methylethoxy-propanol and sodium chloride to the reaction mixture increases overall yield of furfural from corn cob.

TABLE 19

| Run | Reaction Conditions | Solvents | Metal Salt | % Yield Furfural | Xylose | Arabinose | Formic Acid | Total |
|---|---|---|---|---|---|---|---|---|
| 17A | 10% cob + 0.15M H$_2$SO$_4$, 160° C., 30 min | H$_2$O only, no THF | None | 31 | 38 | 8 | 15 | 93 |
| 17B | | H$_2$O only, no THF | 1% NaBr | 38 | 50 | 7 | 18 | 112 |
| 17C | | H$_2$O only, no THF | 1% NiBr$_2$ | 38 | 45 | 6 | 10 | 99 |
| 17D | | H$_2$O only, no THF | 1% CaBr$_2$ | 39 | 51 | 7 | 10 | 108 |
| 17E | | H$_2$O only, no THF | 1% NaCl | 35 | 39 | 6 | 11 | 91 |
| 17F | | H$_2$O only, no THF | 1% NiCl$_2$ | 37 | 40 | 0 | 10 | 87 |
| 17G | | H$_2$O only, no THF | 1% CaCl$_2$ | 35 | 42 | 6 | 10 | 93 |
| 17H | | 50% THF | None | 48 | 19 | 8 | 10 | 85 |
| 17I | | 50% THF | 1% NaBr | 75 | 15 | 8 | 9 | 107 |
| 17J | | 50% THF | 1% NiBr$_2$ | 65 | 13 | 7 | 16 | 101 |
| 17K | | 50% THF | 1% CaBr$_2$ | 75 | 12 | 8 | 17 | 112 |
| 17L | | 50% THF | 1% NaCl | 78 | 4 | 0 | 8 | 91 |
| 17M | | 50% THF | 1% NiCl$_2$ | 72 | 8 | 7 | 13 | 99 |
| 17N | | 50% THF | 1% CaCl$_2$ | 66 | 2 | 3 | 17 | 88 |

TABLE 20

| Run | Reaction Conditions | Solvent System | NaCl Loading | % Yield Furfural | HMF | Xylose | Arabinose | Formic Acid | Total |
|---|---|---|---|---|---|---|---|---|---|
| Comp Ex A | 25% corn cob + 0.15M H₂SO₄, 160° C., 30 min | H₂O only, no 2-methoxy-methylethoxy-propanol | no NaCl | 24 | 1 | 34 | 6 | 3 | 68 |
| Comp Ex A (rep) | | | no NaCl | 24 | 1 | 34 | 6 | 3 | 68 |
| 1C | | | 1% NaCl | 29 | 1 | 26 | 7 | 5 | 67 |
| 1C (rep) | | | 1% NaCl | 30 | 1 | 22 | 6 | 5 | 63 |
| 417 | | 83/17 2-methoxy-methylethoxy-propanol/ H₂O | no NaCl | 40 | ND | 2 | 6 | 11 | 59 |
| 393 | | | 1% NaCl | 56 | 20 | 0 | 2 | 2 | 60 |

What is claimed is:

1. A process comprising:
   a) providing an aqueous solution comprising a metal halide, a water-miscible organic solvent, a mineral acid, and water;
   b) providing a feedstock comprising at least one selected from:
      i) lignocellulosic feedstock containing glucan and xylan,
      ii) hemicellulosic material,
      iii) C₅ sugar monomers and —C₅ oligomers;
   c) contacting the feedstock with the aqueous solution to form a reaction mixture, wherein
      i) the concentration of water-miscible organic solvent is from about 10 weight percent to about 80 weight percent,
      ii) the concentration of metal halide is from about 0.1 weight percent to about 2 weight percent,
      iii) the mineral acid concentration is from about 0.5 to about 4 weight percent; and
      iv) the feedstock is present at about 1 to about 50 weight percent,
   wherein the weight percentages are based on the total weight of the reaction mixture; and
   d) heating the reaction mixture at a temperature in the range of about 140° C. to about 190° C. for a time sufficient to effect a reaction to produce furfural, wherein the aqueous solution remains monophasic at the reaction temperature and at the completion of the reaction.

2. The process of claim 1 wherein the metal halide is an alkali halide.

3. The process of claim 2 wherein the alkali halide is NaCl, NaBr, NaI, or a mixture of two or more thereof.

4. The process of claim 1 wherein the metal halide is an alkaline earth halide.

5. The process of claim 4 wherein the alkaline earth halide is CaCl₂, MgBr₂ or a mixture thereof.

6. The process of claim 1 wherein the metal halide is a transition metal halide.

7. The process of claim 6 wherein the transition metal halide is NiBr₂, MnBr₂, or a mixture of any of these.

8. The process of claim 1 wherein the mineral acid is HCl, H₂SO₄, or HNO₃.

9. The process of claim 1 wherein the water-miscible organic solvent is an ether.

10. The process of claim 9 wherein the ether is THF, dimethyl ether, 2-methoxy-methylethoxy-propanol, or 1,4-dioxane, from about 50 weight percent to about 80 weight percent, based on the weight of the reaction mixture.

11. The process of claim 9 wherein the ether is THF and the concentration of the ether is from about 70 weight percent to about 80 weight percent, based on the weight of the reaction mixture.

12. The process of claim 1 wherein the feedstock comprises one or more selected from the group consisting of: corn cobs, corn husks, corn stover, grasses, wheat, wheat straw, barley, barley straw, hay, rice straw, switchgrass, sugar cane bagasse, sorghum, soy, trees, branches, roots, leaves, wood chips, sawdust, shrubs, bushes, vegetables, fruits, flowers.

13. The process of claim 1 wherein the feedstock comprises corn cob, the metal halide is NaCl, the water-miscible organic solvent is THF and the mineral acid is 1% sulfuric acid.

* * * * *